United States Patent
Nanba et al.

(10) Patent No.: US 6,669,632 B2
(45) Date of Patent: Dec. 30, 2003

(54) APPARATUS AND METHOD FOR ELECTRONICALLY PREDICTING PLEURAL PRESSURE FROM PULSE WAVE SIGNALS

(75) Inventors: Shinji Nanba, Kariya (JP); Rie Ohsaki, Anjo (JP); Toshiaki Shiomi, 31, Terugaoka, Meitoku, Nagoya-city, Aichi-pref., 465-0042 (JP)

(73) Assignees: Denso Corporation, Kariya (JP); Toshiaki Shiomi, Nagoya (JP)

( * ) Notice: Subject to any disclaimer, the term of this patent is extended or adjusted under 35 U.S.C. 154(b) by 84 days.

(21) Appl. No.: 10/101,835

(22) Filed: Mar. 21, 2002

(65) Prior Publication Data

US 2002/0143261 A1 Oct. 3, 2002

(30) Foreign Application Priority Data

Mar. 30, 2001 (JP) .................... 2001-100527
Jan. 28, 2002 (JP) .................... 2002-018403

(51) Int. Cl.[7] .............................. A61B 5/02
(52) U.S. Cl. ............ 600/300; 600/500; 600/529; 600/561
(58) Field of Search ............ 600/300, 485, 600/500–507, 529–543, 561

(56) References Cited

U.S. PATENT DOCUMENTS 4,074,710 A * 2/1978 Tiep ................. 600/502
5,181,517 A * 1/1993 Hickey ............... 600/486
5,385,144 A * 1/1995 Yamanishi et al. ...... 600/330
6,360,123 B1 * 3/2002 Kimchi et al. ......... 600/547

OTHER PUBLICATIONS

Smith et al. "Pulse transit time: an appraisal of potential clinical applications", Thorax 1999; 54:452–458.*
Argod et al. "Comparison of Esophageal Pressur with Pulse Transit Time as a Measure of Respiratory Effort for Scoring Obstructive Nonapneic Respiratory Events", American Journal of Respiratory and Critical Care Medicine 2000; 162:87–93.*
Toshiki Kimura, "Hemodynamics Associated with Sleep Disorders in Anesthetized Dogs", *Second Department of Internal Medicine*, Hiroshima University School of Medicine, Hiroshima, Japan vol. 33(1) 1995 pp. 3–9.

* cited by examiner

*Primary Examiner*—Max F. Hindenburg
*Assistant Examiner*—Patricia Mallari
(74) *Attorney, Agent, or Firm*—Posz & Bethards, PLC (57) ABSTRACT

A pleural pressure is predicted from pleural pressure based upon pulse wave signals, which are continuously produced and picked up in a time sequential manner. A first variation signal indicative of a condition of a variation contained in the pulse wave signals is acquired based upon the pulse wave signals. A second variation signal representative of a condition of a variation contained in the first variation signal is acquired based upon the first variation signal. The pleural pressure is predicted based on a difference between the first variation signal and the second variation signal.

26 Claims, 9 Drawing Sheets

APPARATUS AND METHOD FOR ELECTRONICALLY PREDICTING PLEURAL PRESSURE FROM PULSE WAVE SIGNALS

CROSS REFERENCE TO RELATED APPLICATION

This application is based on and incorporates herein by reference Japanese Patent Applications No. 2001-100527 filed Mar. 30, 2001 and No. 2002-18403 filed Jan. 28, 2002.

FIELD OF THE INVENTION

The present invention is related to a pleural or esophageal pressure predicting apparatus, a medical apparatus, a pleural or esophageal pressure predicting method, a diagnosing method and an examining method, which are capable of diagnosing a sleep apnea syndrome, an upper airway resistance syndrome, and the like, and also capable of evaluating a medical treatment effect, while monitoring, for instance, pleural or esophageal pressure conditions during sleep time.

BACKGROUND OF THE INVENTION

Pleural pressure has close correlation with respect to health conditions of patients, and hence may be effectively used to diagnose closed type apnea syndromes and upper airway resistance syndromes and the like. However, it is practically difficult to measure such pleural pressure. Also, measurements of esophageal pressure which may substitute the above pleural pressure measurements cannot be easily carried out, since sensors should be inserted from nose holes into esophaguses which may give strong pain to patients. Therefore, in actual cases, the above sleep apnea syndromes and upper airway resistance syndromes are diagnosed by monitoring respiration conditions based upon air streams from noses, motion of breasts, motion of venter and the like.

However, in the case of such a diagnosing method by monitoring the respiration conditions based upon the air streams from the noses and the like, it is cumbersome to attach the sensors, or instruments. Furthermore, diagnostic precision of this respiration condition monitoring method is low. As a consequence, development of easier diagnosing methods with higher diagnostic precision has been strongly required in this medical field.

SUMMARY OF THE INVENTION

The present invention has an object to provide a pleural pressure predicting apparatus, a medical apparatus, a pleural pressure predicting method, a diagnosing method, and an examining method, capable of diagnosing a sleep apnea syndrome, an upper airway resistance syndrome, and the like, while pleural pressure can be predicted by way of a simple method without giving loads on patients.

According to the present invention, a pleural or esophageal pressure is predicted from pleural pressure based upon pulse wave signals, which are continuously produced and picked up in a time sequential manner. A first variation signal indicative of a condition of a variation (fluctuations of entire pulse wave signals) contained in the pulse wave signals is acquired based upon the pulse wave signals. A second variation signal representative of a condition of a variation (fluctuations of entire first variation signals) contained in the first variation signal is acquired based upon the first variation signal. The pleural pressure is predicted based on a difference between the first variation signal and the second variation signal.

This is based on a finding that there is a high correlation between a difference between the first variation signal (for example, first envelope) and the second variation signal (for instance, second envelope), and also the pleural pressure indicated by actual esophageal pressure.

The first variation signal shows a condition of variations (fluctuations) of the entire pulse wave signals in which a large number of pulse wave signals are continuously connected to each other. This first variation signal is mainly varied in response to a change contained in pleural pressure. Among signal components of this first variation signal, there are contained external disturbance components (for instance, signal components of autonomic nervous system for controlling blood pressure, for expanding blood vessel, and for compressing blood vessel) other than the pleural pressure.

The second variation signal corresponds to such a signal having a lower frequency (for example, lower than, or equal to 1 Hz) than the frequency of the first variation signal. Also, this second variation signal mainly contains the above external disturbance components. As a result, since the difference between the first variation signal and the second variation signal is calculated, such a signal indicative of only pleural pressure can be derived by eliminating the external disturbance components.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS (First Embodiment)

Figure 1A:
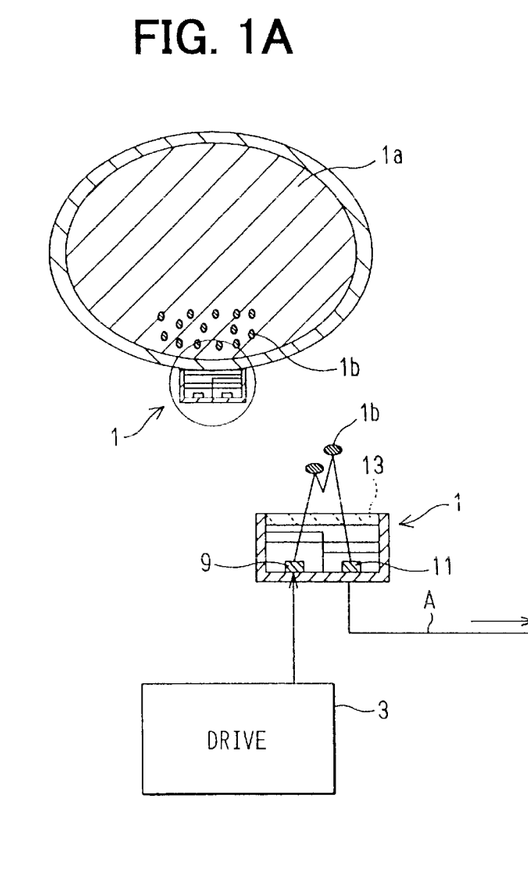
FIG. 1A is a schematic view of a pulse wave sensor used in a medical apparatus equipped with a pleural pressure predicting apparatus according to the first embodiment of the present invention.
Figure 1B:
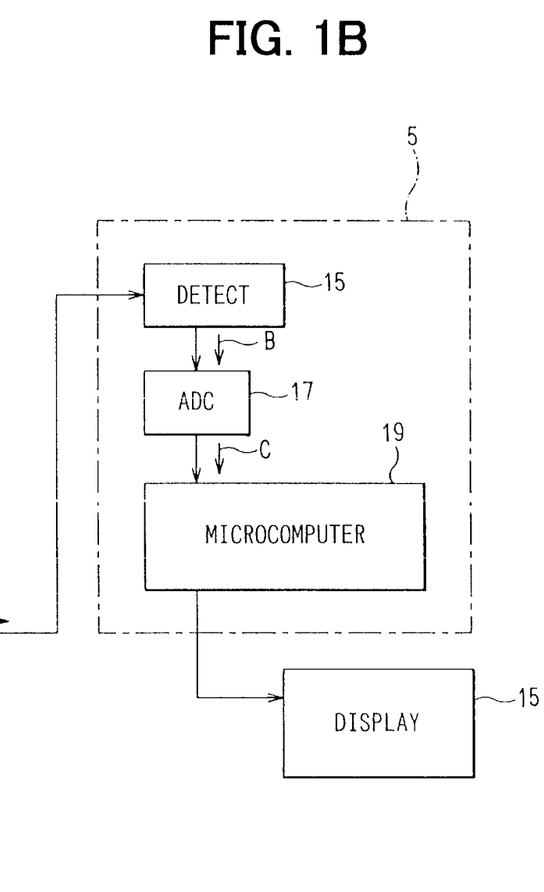
FIG. 1B is an electric wiring diagram of the medical apparatus according to the first embodiment.

Referring first to FIGS. 1A and 1B, a medical apparatus is provided with a pulse wave sensor 1, a drive circuit 3, a data processing unit 5, and a display device 7. The pulse wave sensor 1 is used by being mounted on such a place of a human body 1a, for example, a rear side portion of a wrist, the movement of which is small. The drive circuit 3 electrically drives the pulse wave sensor 1. The data processing unit 5 measures human pulse waves based upon a measurement result outputted from the pulse wave sensor 1 to calculate a pulse interval, a pulse fluctuation, and the like. The display device 7 displays thereon a processed result obtained from the data processing unit 5.

Figure 2:
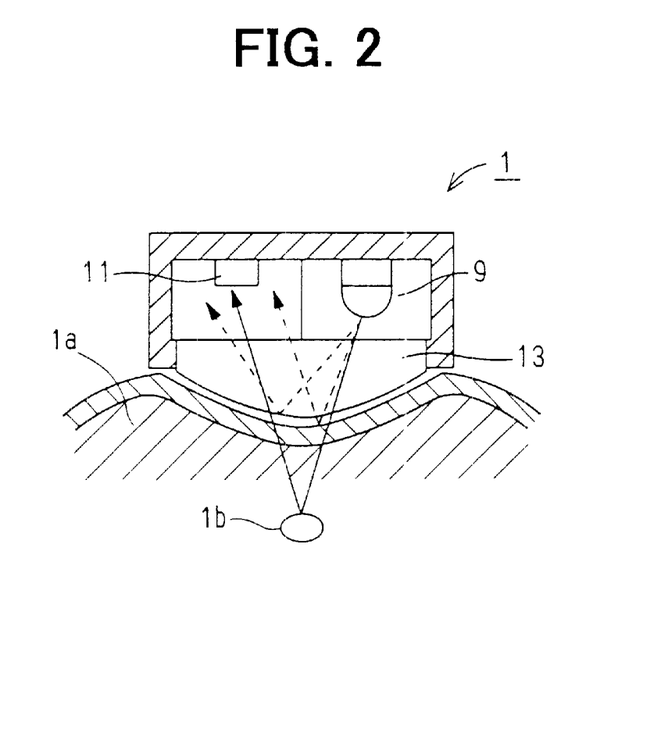
FIG. 2 is a sectional view of the pulse wave sensor used in the first embodiment.

As shown in FIG. 2, the pulse wave sensor 1 is an optical type reflection mode sensor equipped with a light emitting element (for instance, green LED) 9, a light receiving element (for example, photodiode) 11, a transparent lens body 13, and the like. The transparent lens body 13 may penetrate therethrough light, and may receive light in high efficiency.

This pulse wave sensor 1 has a higher S/N ratio of 1/60 than that of the conventional pulse wave sensor, and amplifies all of frequencies of pulse waves, namely, performs a DC amplification. This S/N ratio implies a ratio of a signal component "S" to a total light receiving amount "N" in conjunction with a volume change of bloods. As a result, this pulse wave sensor 1 may acquire not only a pulse wave number, but also an activity of an autonomic nerve system which controls a heart beat number, and furthermore, may acquire most of such information contained in pulse waves such as a respiration condition and a blood vessel condition.

When light is irradiated from the light emitting element 9 to the human body 1a by supplying electric drive power from the drive circuit 3, a portion of this light is lightened on a blood capillaries 1b which runs inside the human body 1a. Then, the light is absorbed by mainly hemoglobin contained in blood flowing through each blood capillary 1b. The remaining light is repeatedly scattered, and then, a portion of this scattering light enters into the light receiving element 11. At this time, since the amount of hemoglobin in the blood capillary 1b is changed in a wave motion manner by pulsatory move of the blood, light which is to be absorbed by the hemoglobin is also changed in a wave motion manner.

Figure 3:
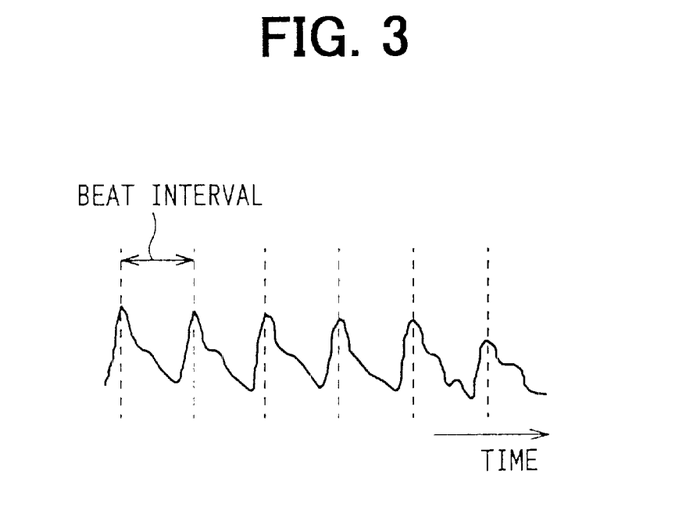
FIG. 3 is a signal waveform chart graphically showing a waveform of a pulse wave signal.

As a result, since the amount of light absorbed by the blood capillary 1b changes, the amount of such light detected by the light receiving element 11 changes, so that this change in the light receiving amount is outputted from this pulse wave sensor 1 to the data processing unit 5 as pulse wave information (that is, sensor output A corresponding to voltage signal indicative of pulse wave). The exemplary waveform pattern of this sensor output signal A is shown in FIG. 3.

On the other hand, the data processing unit 5 has a detecting circuit 15, an A/D converter (ADC) 17 and a microcomputer 19. The detecting circuit 15 amplifies the sensor output A. The A/D converter 17 converts a detected analog signal B indicative of the pulse wave amplified by the detecting circuit 15 into a digital signal C. The microcomputer 19 processes the digital signal C to predict the pleural pressure and the like.

The microcomputer 19 corresponds to such an electronic circuit provided with a CPU, a ROM, a RAM, and the like, which are well known in this technical field. A computer program used to process the digital signal C obtained from the ADC 17 is stored in this microcomputer 19. This program is made based upon an algorithm by which the signal indicative of the pulse wave detected by the pulse wave sensor 1 is processed to predict the pleural pressure, and to diagnose and examine both the sleep apnea syndrome and the upper airway resistance syndrome.

Figure 4:
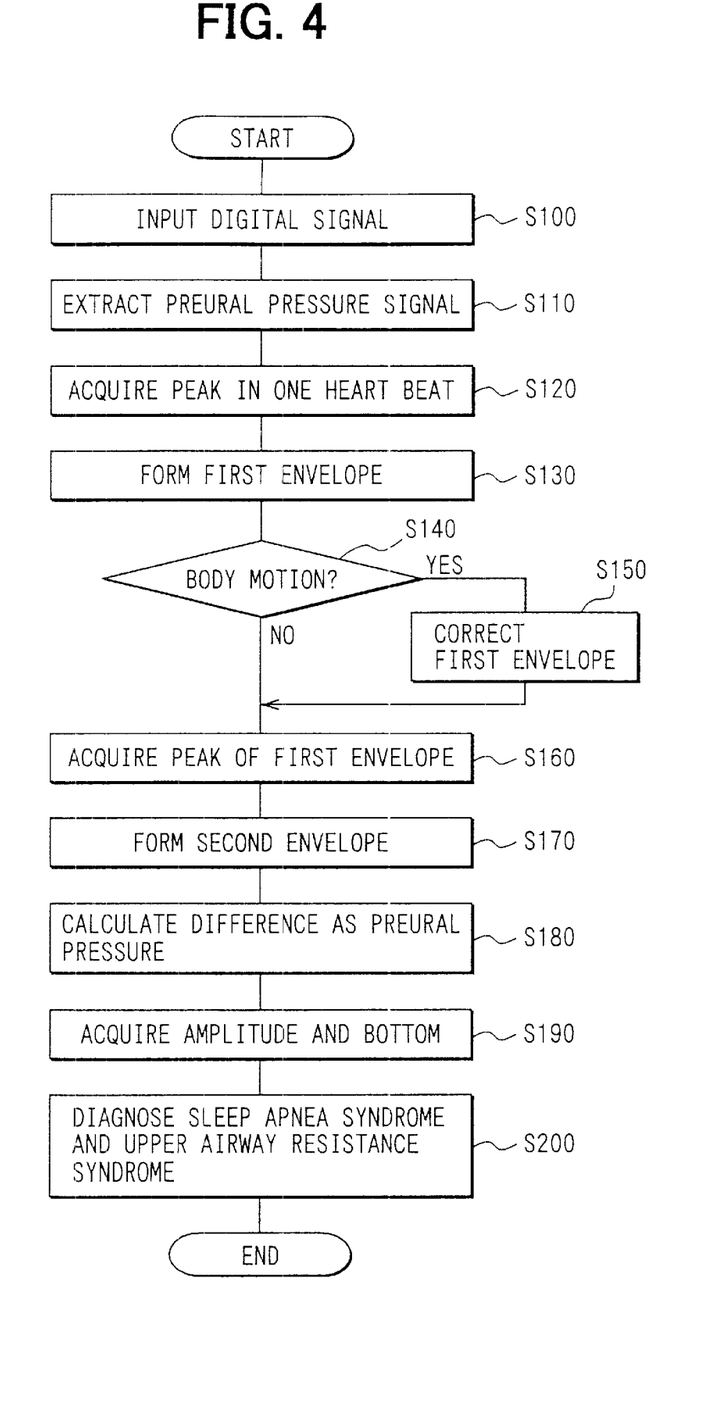
FIG. 4 is a flow chart of processing for predicting pleural pressure and of diagnosing patient conditions, executed in the first embodiment.

The microcomputer 19 is programmed to execute the processing shown in FIG. 4.

(1) Major Processing Operation:

As shown in FIG. 4, the microcomputer 19 executes an input of the pulse wave at step S100. For instance, the digital signal C is inputted into the microcomputer 19. At step S110 subsequent to this step S100, the microcomputer 19 executes a digital filtering processing in order to extract a pleural pressure signal. In order to extract the pleural pressure signal which is reflected on the pulse wave from this digital signal C, both such noise having frequencies higher than, or equal to 3 Hz due to external disturbance noise, and also signals having frequencies lower than, or equal to 0.1 Hz (namely, lower frequencies from that of pleural pressure signal), which are caused by body motion (motion artifact), are cut off.

Then, the microcomputer 19 executes processing capable of extracting a feature of the pulse waveform acquired in the previous step S110, and for producing a numeral value from this extracted feature. In this case, a method for extracting a feature of a waveform (pulse wave waveform) of a pulse wave signal by employing a variation (fluctuation) of this pulse wave signal is described.

Figure 5:
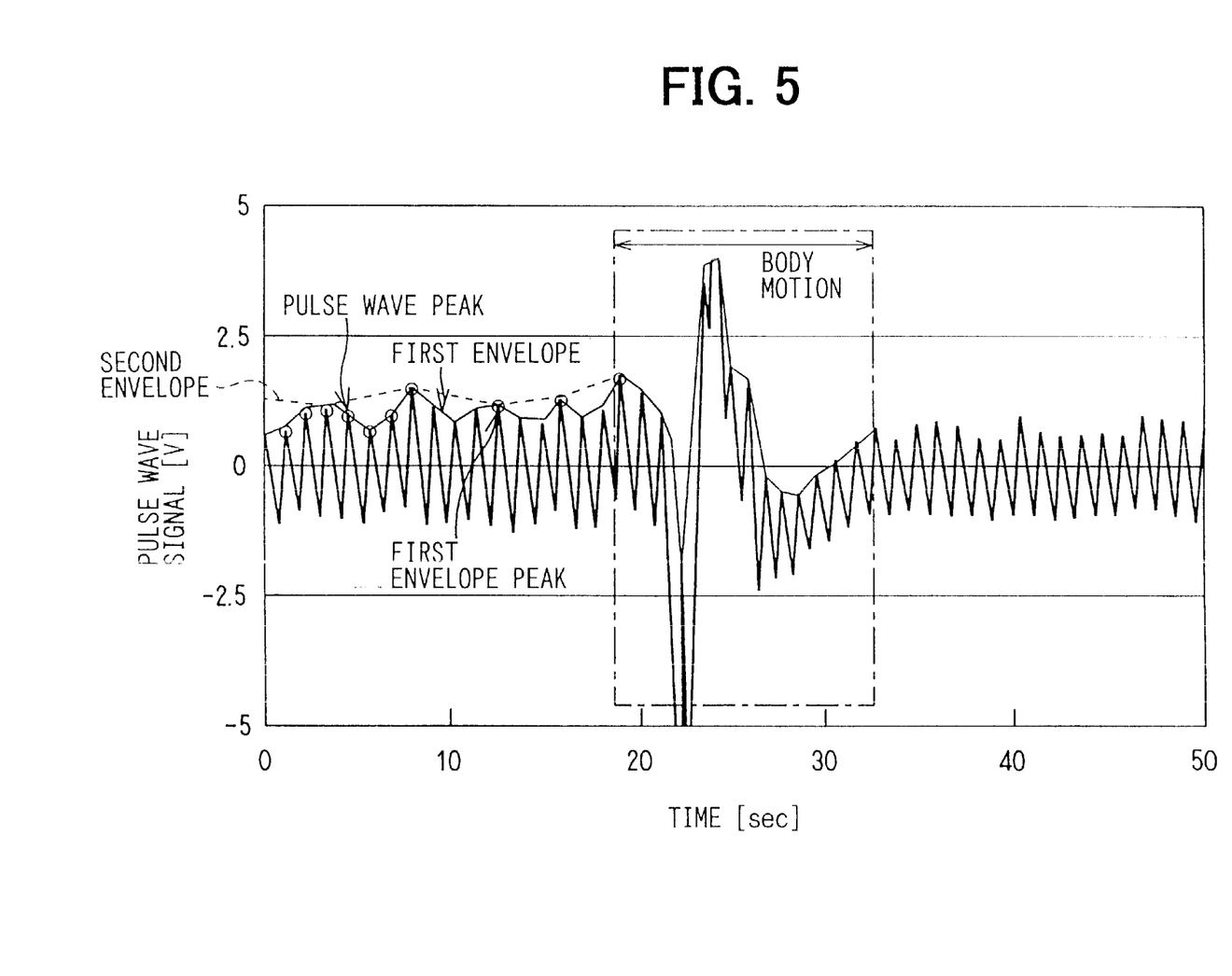
FIG. 5 is a signal waveform chart graphically showing both a pulse wave signal and an envelope thereof.

As indicated in FIG. 5, peaks of the pulse wave of one heart beat are acquired at step S120. It should be understood that FIG. 5 shows a temporal change of signal outputs of pulse waves, and an ordinate indicates a magnitude of an output of a pulse wave signal from a reference value (0). At the subsequent step S130, the respective peaks acquired in the previous step S120 are connected to each other to form a first envelope as shown in FIG. 5.

At the next step S140, the microcomputer 19 checks whether or not body motion is present. In the case of presence of the body motion, the processing is advanced to a step S150. To the contrary, in the case of no body motion, the processing is advanced to another step S160.

At step S150, since the body motion is present, the first envelope after the body motion (after end of body motion) is corrected by executing a method of correcting an envelope to remove an adverse influence of this body motion from the first envelope formed at step S130. In the case that the body motion is present, pulse wave signals appearing during a time duration of the body motion indicated by a dot and dash line in FIG. 5 are cut off and are not used.

On the other hand, at step S160, peaks of the first envelope which is obtained when the body motion is not present at step S130 are acquired, or peaks of the first envelop which is obtained by the correction made in the case that the body motion is present at step S150 are acquired. At the next step S170, the respective peaks of the first envelope are connected to each other to form a second envelope indicated by broken line in FIG. 5. At the subsequent step S180, the microcomputer 19 calculates a difference between the first envelope and second envelope, and then sets this difference as a pleural pressure signal.

At the subsequent step S190, both an amplitude and a bottom of this pleural pressure signal are acquired. This amplitude of the pleural pressure signal indicates a variation of pleural pressure, and this bottom thereof shows pleural pressure when air is sucked.

At the subsequent step S200, the microcomputer 19 diagnoses both the sleep apnea syndrome and the upper airway resistance syndrome by employing both the amplitude and the bottom of the pleural pressure signal acquired in the previous step S190. Then, this processing is once finished. The pleural pressure and diagnostic results are displayed on the display device 7.

(2) Method for Predicting Pleural Pressure:

In this embodiment, the pleural pressure is predicted as follows.

Figure 6A:
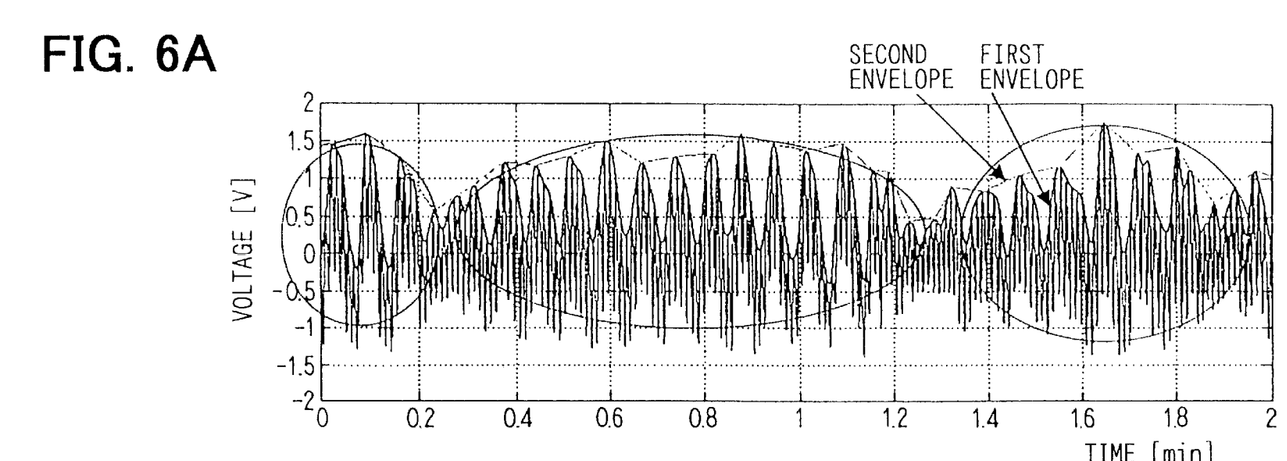
FIG. 6A is a signal waveform chart graphically showing both a first envelope and a second envelope.

As described above, the pulse wave signal is detected in which waveforms of individual signals corresponding to the respective pulse waves are continued, and peaks (namely, upper peaks in this case) of respective waveforms of this pulse wave signal are connected to each other in order to acquire the first envelope. As shown in FIG. 6A, this first envelope has such a waveform which is varied in connection with a change in time. It should be noted that an ordinate of this figure shows a voltage [V] and an abscissa thereof represents time [minute].

Next, peaks (upper peaks in this case) of the respective waveforms of the varied first envelope are connected to each other to acquire the second envelope. As shown in this figure, while this second envelope has waveforms which are varied in connection with a change in time, a frequency of this second envelope is lower than the frequency of the first envelope, and also represents a small variation.

Figure 6B:
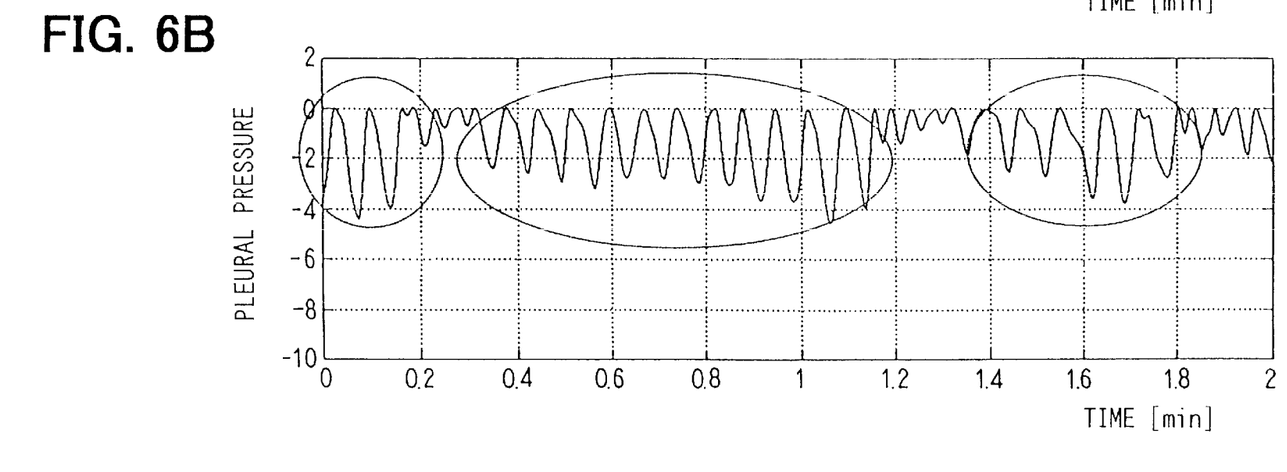
FIG. 6B is a signal waveform chart graphically showing a pleural pressure signal acquired from a difference between the first and second envelopes.

Next, the second envelop is subtracted from the first envelop to obtain a difference signal corresponding to the pleural pressure signal, as represented in FIG. 6B. It should be understood that a pleural exponent of an ordinate of this figure implies a value indicative of pressure, and an abscissa thereof shows time [minute].

It is confirmed by the inventors that the waveform of this difference signal is largely changed (namely, amplitude of waveform is increased) during each apnea condition indicated with circles in FIGS. 6A and 6B. As a result, the apnea condition can be diagnosed based upon the difference signal. As a consequence, both the sleep apnea syndrome and the upper airway resistance syndrome can be diagnosed from the difference signal.

Figure 7:
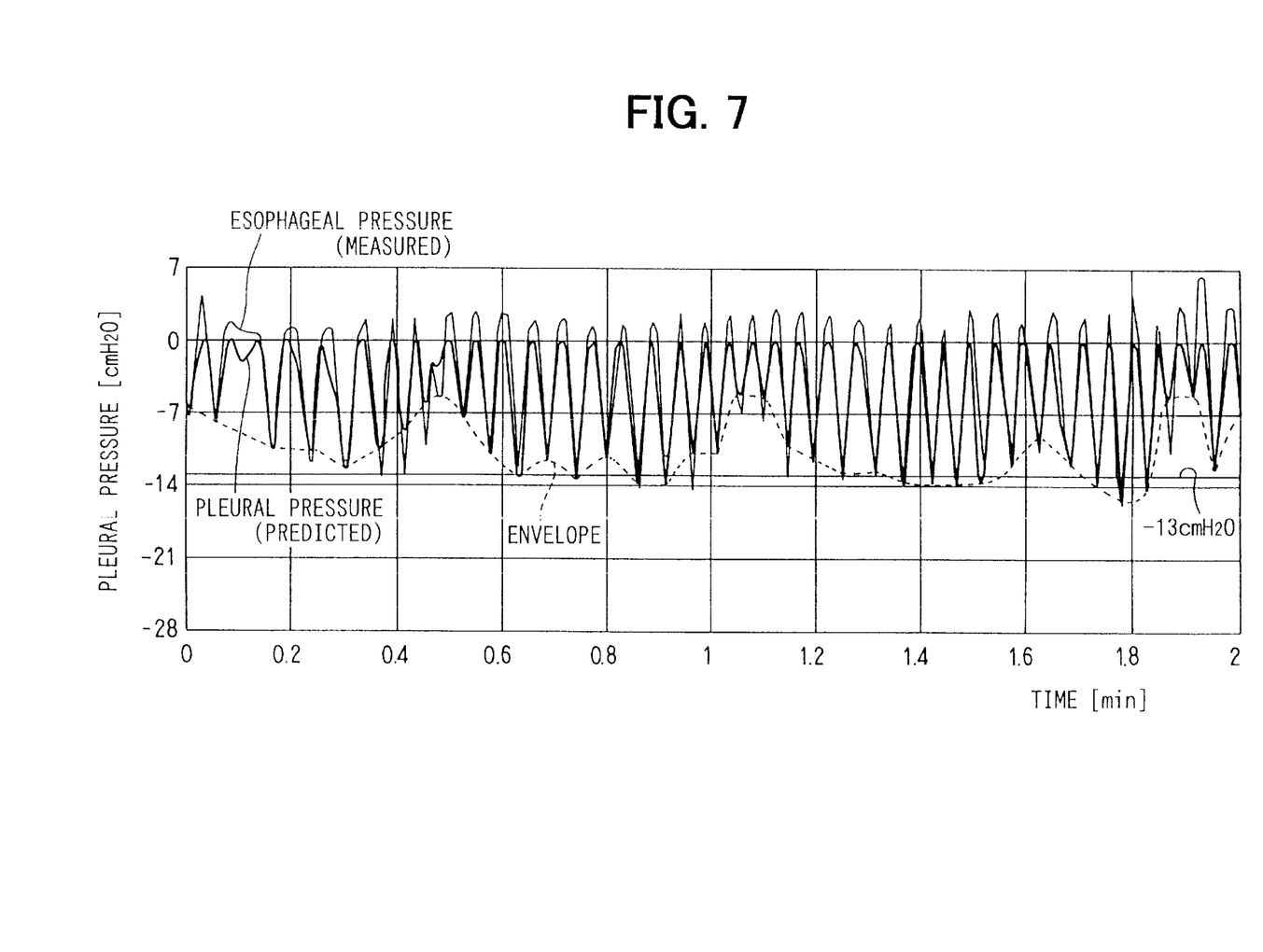
FIG. 7 is a signal waveform chart graphically showing a correlative relationship between pleural pressure measured from a pulse wave and an actually-measured esophageal pressure value.

Also, it is confirmed by the inventors that a correlative relationship shown in FIG. 7 holds between an actually-measured esophageal pressure value indicative of actual pleural pressure, and the predicted pleural pressure value (difference between the first envelope and the second envelope. As a consequence, this difference may be regarded as such a signal indicative of pleural pressure (pleural pressure signal).

Figure 8:
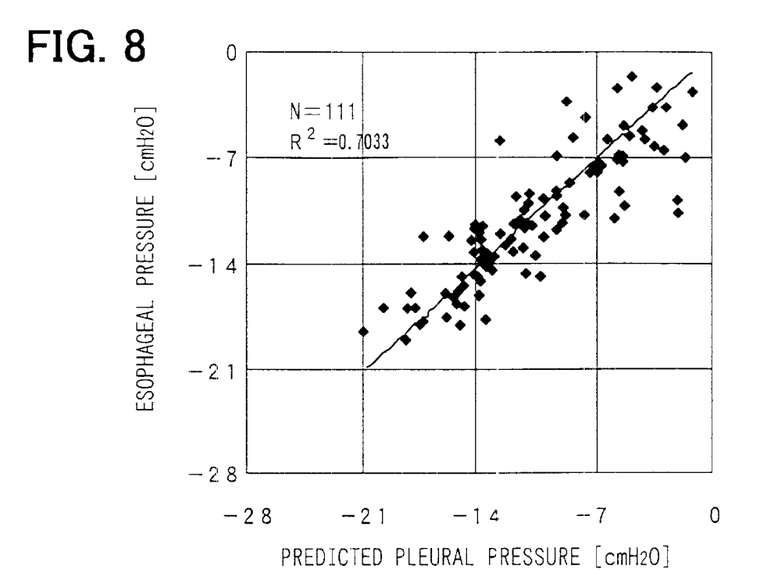
FIG. 8 is a graph graphically indicating a correlative relationship between pleural pressure measured from a pulse wave and an actually-measured pleural pressure by an esophageal pressure sensor.

Furthermore, it is confirmed by the inventors that such a correlative relationship (correlative coefficient R=0.85, $R^2$=approx. 0.7) shown in FIG. 8 holds between the actually-measured esophageal pressure value indicative of actual pleural pressure, and the pleural pressure predicted by the difference between the first envelope and the second envelope. As a consequence, this difference may be regarded as such a signal indicative of pleural pressure (pleural pressure signal). It should be noted that a total data number N in this testing is 111.

(3) Method of Detecting Body Motion:

Next, the method of detecting the body motion executed in the step S140 will now be explained.

As to a measuring portion of a pulse wave by the pulse wave sensor 1, such a portion having small motion as a wrist, an arm, a foot, and a forehead is suitable in view of a measurement stability, and furthermore, in views of attachability of this pulse wave sensor 1. The optimum measuring portion is a rear-sided portion of a wrist in view of the attachability of the pulse wave sensor 1.

In general, a pulse wave is measured at a finger tip portion. While pulse waves are measured at such a finger tip portion, waveforms of these pulse waves are strongly changed due to temperatures of this finger tip portion, and the mounting characteristic (depression pressure of detecting unit), and motion. As a result, this measuring operation at the finger tip portion is not always properly carried out. Also, such a place whose motion is large as an inner portion of a wrist where a tendon is present is not preferable.

However, even when pulse waves are measured on a rear side of a wrist, there are some possibilities that wave heights of the pulse waves are changed. In most cases, a change of body attitudes (body motion) may occur in connection with these wave heights. As a result, a body motion signal is superimposed on these pulse waves. Accordingly, detection of such a body motion is important.

Figure 9:
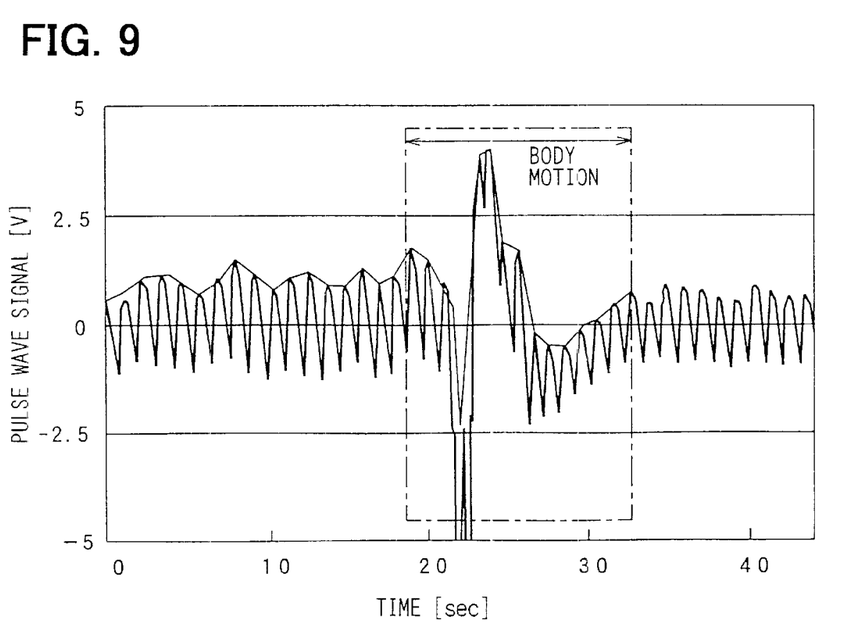
FIG. 9 is a signal waveform chart graphically showing a variation condition of pulse waves caused by body motion.

As a consequence, as shown in FIG. 9, in this embodiment, the amplitude of the first envelope is measured. When this amplitude of the envelope is increased (for example, 3 times, or more larger than average value of previously-measured amplitudes), the microcomputer 19 determines that body motion started. Also, in such a case that the large amplitude of the envelope is returned to be decreased (for instance, 1.2 times, or more smaller than average value of amplitudes measured before body motion is commenced), the microcomputer 19 determines that the body motion disappeared.

(4) Method of Correcting Envelope:

When a body motion occurs, since a body motion signal caused by the occurrence of this body motion is superimposed on a pulse wave signal, an adverse influence thereof is required to be eliminated. As a consequence, in this embodiment, at a time instant when a body motion signal appears, a pleural pressure signal is corrected at step S150 in FIG. 4 based upon wave heights of pulse waves existing before/after this time instant under stable conditions.

Figure 10:
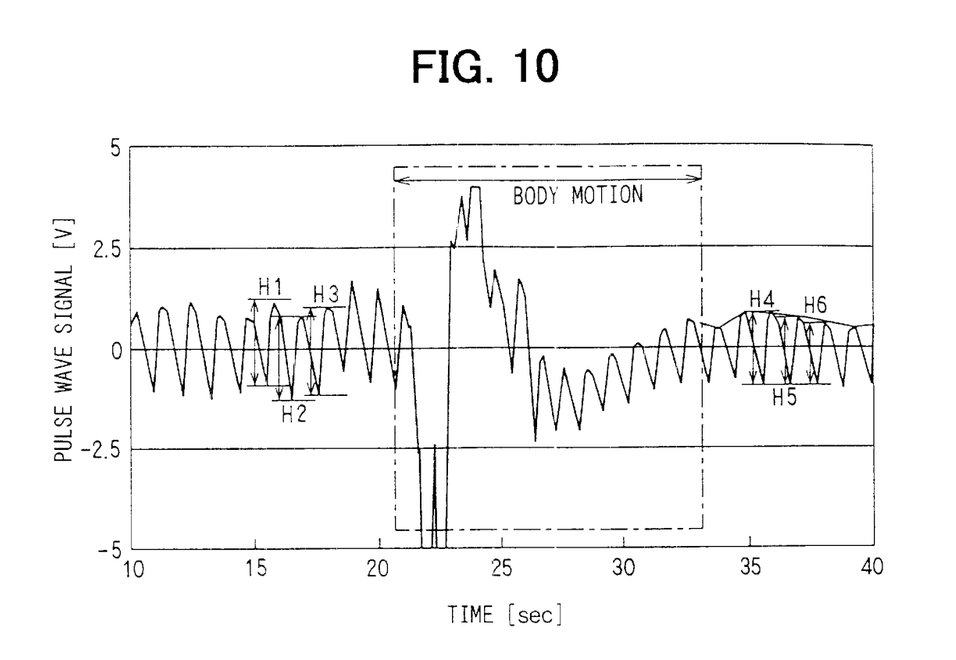
FIG. 10 is a signal waveform chart showing a correction method for removing an adverse influence of the body motion from the pulse waves.

More specifically, as shown in FIG. 10, an average wave height Havb of wave heights H1 to H3 of three heart beats to five heart beats before such a time period during which body motion appears is calculated based upon the following equation (1):

$$Havb=(H1+H2+H3)/3 \qquad (1)$$

Similarly, an average wave height Hava of wave heights H4 to H6 of three heart beats to five heart beats after body motion disappears is calculated based upon the following equation (2):

$$Hava=(H4+H5+H6)/3 \qquad (2)$$

Then, as defined in the following equation (3), while the average wave height Havb before the body motion is used as a reference, the pleural pressure signal is corrected based upon an increase/decrease ratio of the average wave height Hava after the body motion:

corrected envelope after appearance of body motion=(envelope acquired in step S130)×(Havb/Hava) (3)

Thus, after the body motion appears, such an envelope of the pulse wave signal which is obtained by performing the correction at step S150 of FIG. 4 may be used as the first envelope. That is, the above envelope obtained in the equation (3) is used as the first envelope.

(5) Diagnosing Method:

Diagnosing at step S200 is executed as follows with respect to both the sleep apnea syndrome and also the upper airway resistance syndrome.

At a time instant when the envelope produced by connecting the bottoms of the pleural pressure signal shown in FIG. 7 decreases gradually and then reaches a predetermined value (for example, −13 cmH$_2$O), the microcomputer 19 determines this state as a closed type apnea syndrome. In the case that the total number of this reaching operation becomes larger than, or equal to 5 times per one hour, the microcomputer 19 determines this state as a sleep apnea syndrome.

Also, under such a case that the total time of closed type apnea is smaller than, or equal to 5 times per hour which is checked by a sleep polygraph, when the pleural pressure prediction value predicted by the above method is decreased lower than, or equal to a predetermined value, there are many possibilities that the upper airway resistance syndrome occurs. Therefore, the diagnosis executed by employing the pulse wave sensor 1 is additionally carried out in conjunction with the sleep polygraph and the like.

(6) Calibration Method:

The pleural pressure signal produced from the pulse wave indicates not an absolute value of the pleural pressure, but a relative value of the same. As a result, when an absolute value is desired, a calibration should be carried out.

As this calibration manner, for example, while constant pressure (for instance, 20 cmH$_2$O) is applied to a mouth, or a nose of a patient by employing a respirator such as CPAP, the pleural pressure which is actually predicted by the pulse waves may be calibrated. Also, while a pressure control valve is provided at an air intake port of an air intake mask, constant negative pressure is produced when air is sucked. Then, the pleural pressure value may be calibrated which is predicted by pulse waves appearing under this negative pressure. Furthermore, while a pressure sensor is mounted on the above air intake mask, the pulse wave prediction value may be calibrated based upon a pressure value obtained form this pressure sensor. It should be understood that while these calibrations are carried out, the pleural pressure value is normalized as the average wave height of the pulse waves. That is, when the sensor depression force is changed, the pulse waves are increased, or decreased. Otherwise, the pleural pressure signal is increased, or decreased in proportional to this depression pressure change. Therefore, this value is divided by the average wave height to be corrected.

As described above, the microcomputer 19 processes the pulse wave signals acquired by the pulse wave sensor 1, so that the difference is calculated between the first envelope indicative of the variation of the pulse wave signals and the second envelope representative of the variation of the first envelope signal. As a result, the pleural pressure can be correctly predicted by this calculated difference. As a consequence, in comparison with the conventional method for directly measuring the esophageal pressure, the pleural pressure can be predicted by way of the very simple manner without giving the loads to the patient.

Furthermore, when the above difference is calculated, it is checked whether or not the body motion is present. When such a body motion appears, the correction is carried out by eliminating the adverse influence caused by this body motion from the pulse wave signal. As a consequence, there is an advantage that the pleural pressure can be correctly acquired in view of this correction.

Moreover, while the pleural pressure acquired from the pulse waves is employed, such a diagnostic operation as to the sleep apnea syndrome and the upper airway resistance syndrome can be carried out by executing a computerized diagnosis, the cumbersome diagnosing works can be reduced, and the diagnostic precision can be improved.

(Second Embodiment)

In this second embodiment, a first amplitude ratio line (respiration curve) is employed instead of the above first envelop used in the first embodiment.

Figure 11:
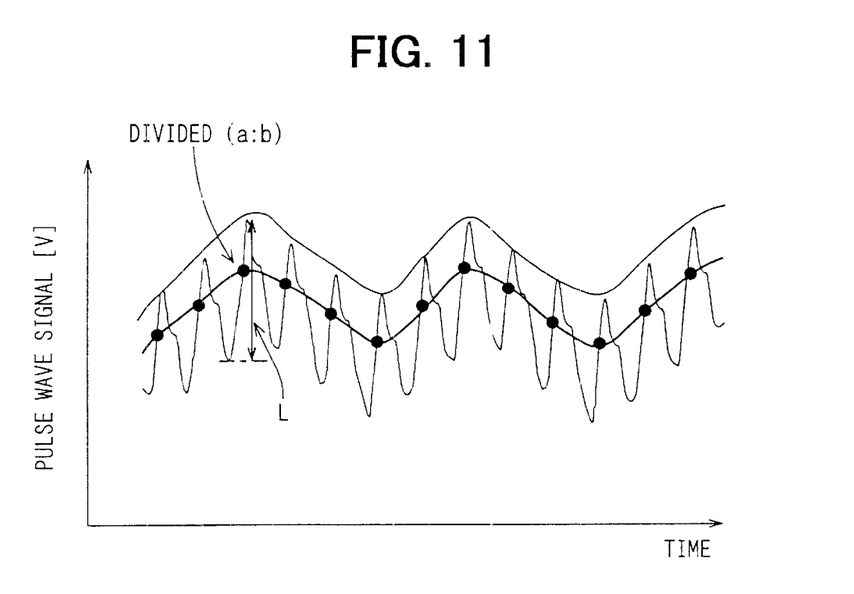
FIG. 11 is a signal waveform chart showing graphically a pleural pressure predicting method, which uses an amplitude ratio line, according to the second embodiment of the present invention.

In accordance with this embodiment, as shown in FIG. 11, amplitudes (L) of the respective waveforms of a pulse wave signal are divided by an average wave height to be corrected. Such points that the amplitudes are subdivided by a predetermined ratio (for example, arbitrary ratio of a:b) are connected to each other to acquire a first amplitude ratio line (respiration curve) indicative of a variation condition of the pulse wave signals.

Furthermore, such points that the amplitudes are subdivided by a predetermined ratio (for example, arbitrary ratio of a:b) are connected to each other to acquire a second amplitude ratio line indicative of a variation of the first amplitude ratio line.

Thereafter, the second amplitude ratio line is subtracted form the first amplitude ratio to obtain a difference signal (namely, pleural pressure signal). Then, pleural pressure may be predicted based upon this pleural pressure signal in the similar manner as in the first embodiment.

Also, in this second embodiment, since the pleural pressure signal acquired by executing the above method corresponds to the pleural pressure, the pleural pressure can be predicted from this pleural pressure signal similar to the first embodiment. Also, in accordance with this second embodiment, the diagnosing operation as to either the sleep apnea syndrome or the upper airway resistance syndrome can be carried out.

It should also be noted that various methods other than the above method of the second embodiment may be carried out. That is, (1) while peaks of the respective waveforms of the first amplitude ratio line are connected to each other in order to obtain the second envelope, the pleural pressure signal may be acquired based upon the difference between the first amplitude ratio line and the second envelope. Alternatively, (2) while such points that the amplitudes of the respective waveforms of the first envelope are subdivided by a preselected ratio are connected to each other in order to obtain the second amplitude ratio line, the pleural pressure signal may be acquired based upon the difference between the first envelope and the second amplitude ratio line. Also, although precision is lowered, a frequency component (approximately 0.25 Hz) of respiration is extracted from the pulse wave signal by using a band-pass filter. Then, even when a fluctuation of this extracted signal along an amplitude direction is used as the pleural pressure signal, a similar effect may be achieved.

(Third Embodiment)

In this third embodiment, the body motion checking method is different from that of the first embodiment. That is, in this embodiment, the body motion checking is carried out based upon a result of a frequency analysis of the pulse waveform shown in FIGS. 12A and 12B. In those figures, the ordinate denotes a power spectrum calculated by FFT normal, and the abscissa denotes a frequency [Hz].

Figure 12A:
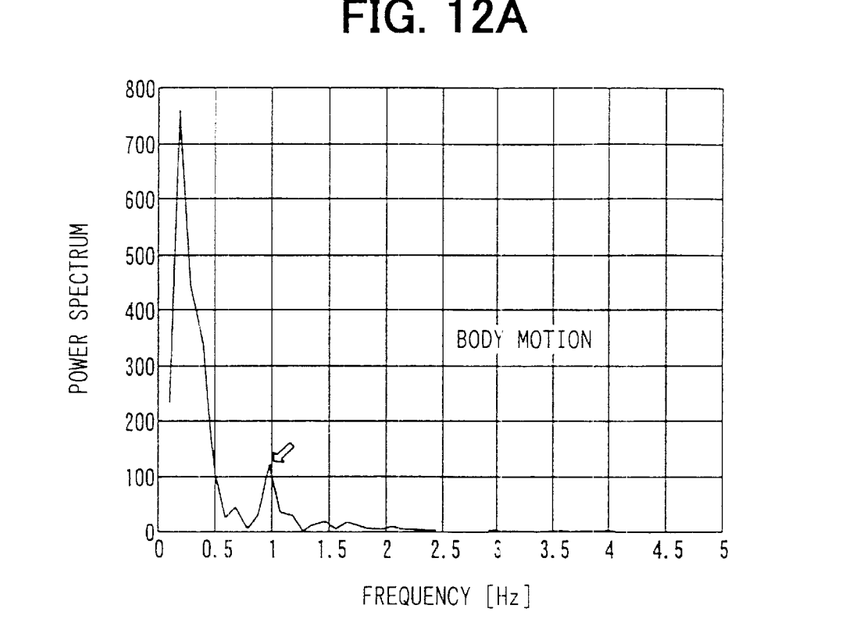
FIGS. 12A and 12B are graphs graphically showing a variation condition of frequency components contained in pulse waves, caused by body motion, according to the third embodiment of the present invention.
Figure 12B:
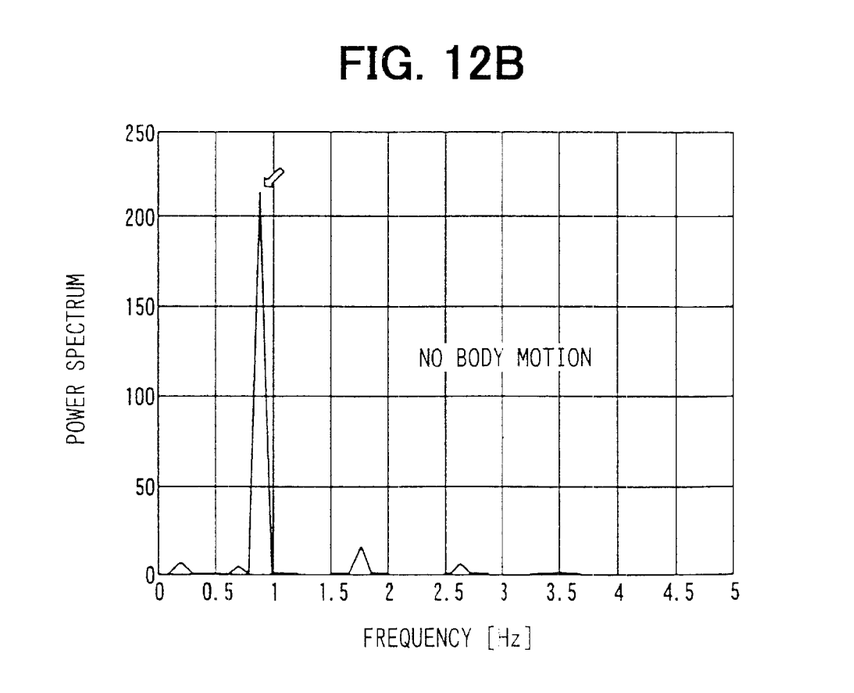

It was found by the inventors that, in the case the body motion is not present, as shown in FIG. 12B, a peak is present in a frequency (on the order of 1 Hz) of a pulse interval. However, in the case the body motion is present, as shown in FIG. 12A, the peak of the frequency of the pulse interval becomes low.

As a consequence, for instance, in the case that the power of the frequency of the pulse interval (on the order of 1 Hz) becomes lower than, or equal to $2/3$ thereof, it can be regarded that the body motion appeared. Then, at a time instant when this lowered power rises again to such power obtained before the body motion occurs, it can be determined that the body motion disappeared.

(Fourth Embodiment)

This fourth embodiment is directed to an examining method capable of confirming a medical treatment effect.

In a case that a certain medical treatment (for instance, high pressure is applied by using CPAP) is carried out with respect to either a patient of a sleep apnea syndrome or a patient of an upper airway resistance syndrome, the medical treatment effect may appear as the above change in the pleural pressure. As a consequence, since this change in the pleural pressure is measured, the medical treatment effect can be confirmed.

For example, while CPAP is employed, when such a medical treatment is carried out by forcibly applying respiration pressure higher than the normal respiration pressure, the medical treatment effect thereof can be confirmed from a change in pleural pressure, which is caused by this medical treatment.

That is, in a case that a medical treatment for applying air (or oxygen) which is pressured by using, for example CPAP is carried out with respect to either a patient of a sleep apnea syndrome or a patient of an upper airway resistance syndrome, if such pleural pressure which is approximated to the normal pleural pressure can be acquired, then such a determination can be made. That is, the medical treatment effect with respect to the patient of either the sleep apnea syndrome or the upper airway resistance syndrome can be achieved.

Also, if the pleural pressure can be grasped, then the applied pressure which is pressured by, for example, CPAP is controlled to be set to optimum pressure. As a consequence, more effective medical treatment effects may be achieved.

It should also be understood that the present invention is not limited to the above embodiments, but may be modified, changed or substituted without departing from the technical scope and spirit of the present invention.

For instance, while the data acquired from the pulse wave sensor may be transmitted to a data processing unit installed at a remote place by utilizing a communication line, for instance, the Internet, and then, this transmitted data is used to execute the diagnosing operation and the examining operation. Furthermore, once the signal acquired by the pulse wave sensor is stored in a storage medium, both the diagnosing operation and the examination may be carried out by using the data stored in this recording medium after several days.

Furthermore, in place of using the set of the first and second envelops or the set of the first and second amplitude ratio lines, other various methods may be employed which indicates, for example, a variation of original signal waveforms such as a line produced by connecting such points to each other, while these points are lower than the peaks of the respective waveforms by a preselected value.

What is claimed is:

1. A pressure predicting apparatus for predicting pleural or esophageal pressure based upon pulse wave signals which are continuously connected to each other in a time sequential manner, the apparatus comprising:

first means for acquiring a first variation signal indicative of a condition of a variation contained in the pulse wave signals based upon the pulse wave signals;

second means for acquiring a second variation signal representative of a condition of a variation contained in the first variation signal based upon the first variation signal; and prediction means for predicting a pleural pressure based on a difference between the first variation signal and the second variation signal.

2. The pressure predicting apparatus as set forth in claim 1, wherein the first variation signal corresponds to a first envelope produced by connecting peaks of waveforms to each other as to a signal indicative of respective pulse waves.

3. The pressure predicting apparatus as set forth in claim 1, wherein the first variation signal corresponds to a first amplitude ratio line produced by connecting points to each other, which are obtained by dividing an amplitude of a waveform of a signal indicative of respective pulse waves by a predetermined ratio.

4. The pressure predicting apparatus as set forth in claim 1, wherein the second variation signal corresponds to a second envelope produced by connecting peaks of respective waveforms in the first variation signal to each other.

5. The pressure predicting apparatus as set forth in claim 1, wherein the second variation signal corresponds to a second amplitude ratio line produced by connecting points to each other, which are obtained by dividing amplitudes of respective waveforms in the first variation signal by a predetermined ratio.

6. The pressure predicting apparatus as set forth in claim 1, wherein the pulse waves are measured at one of a rear side of a wrist, a shin of a foot or a forehead whose motion is small.

7. The pressure predicting apparatus as set forth in claim 1, further comprising:
calibration means for carrying out a calibration of the pleural pressure based upon either pulse wave data acquired during respiration while setting preselected pressure to both a nose and a mouth, or both air-sucking negative pressure generated by way of a sucking action and pulse wave data acquired by the air sucking action.

8. The pressure predicting apparatus as set forth in claim 1, further comprising:
motion detection means for detecting a body motion from the variation condition of the pulse wave signals.

9. The pressure predicting apparatus as set forth in claim 8, further comprising:
correcting means for correcting the predicted pleural pressure by the body motion detected from the pulse wave signals.

10. The pressure predicting apparatus as set forth in claim 8, wherein the motion detection means analyzes frequencies of the pulse wave signals to detect the body motion.

11. A medical apparatus, wherein a diagnosing operation as to one of a sleep apnea syndrome and an upper airway resistance syndrome is carried out by employing the pressure predicted by the pressure predicting apparatus as set forth in claim 1.

12. A medical apparatus, wherein a medical treatment effect as to one of a sleep apnea syndrome and an upper airway resistance syndrome is confirmed by employing the pressure predicted by the pressure predicting apparatus as set forth in claim 1.

13. A pressure predicting method for predicting pleural or esophageal pressure based upon pulse wave signals, which are continuously connected to each other in a time sequential manner, the method comprising steps of:

acquiring a first variation signal indicative of a condition of a variation contained in pulse wave signals;

acquiring a second variation signal representative of a condition of a variation contained in the first variation signal; and predicting a pleural pressure based on a difference between the first variation signal and the second variation signal.

14. A program comprising:
means for realizing a function of the pressure predicting apparatus as set forth in claim 1.

15. A diagnosing method executed by a computer, wherein a diagnosing operation as to a sleep apnea syndrome or an upper airway resistance syndrome is carried out by employing the pressure predicted by the pressure predicting method as set forth in claim 13.

16. A program comprising:
means for realizing a function of the medical apparatus as set forth in claim 11.

17. The pressure predicting method as set forth in claim 16, wherein the first variation signal corresponds to a first envelope produced by connecting peaks of waveforms indicative of the pulse wave signals to each other.

18. The pressure predicting method as set forth in claim 16, wherein the first variation signal corresponds to a first amplitude ratio line produced by connecting points to each other, which are obtained by dividing an amplitude of a waveform of a signal indicative of respective pulse waves by a predetermined ratio.

19. The pressure predicting method as set forth in claim 13, wherein the second variation signal corresponds to a second envelope produced by connecting peaks of the respective waveforms in the first variation signal to each other.

20. The pressure predicting method as set forth in claim 13, wherein the second variation signal corresponds to a second amplitude ratio line produced by connecting points to each other, which are obtained by dividing amplitudes of respective waveforms in the first variation signal by a predetermined ratio.

21. The pressure predicting method as set forth in claim 13, wherein the pulse waves are measured at one of a rear side of a wrist, a shin of a foot or a forehead, whose motion is small.

22. The pressure predicting method as set forth in claim 13, further comprising the step of:
carrying out a calibration of the pressure based upon either pulse wave data acquired during respiration while setting preselected pressure to both a nose and a mouth, or both generating a negative pressure and acquiring pulse wave data during respiration and pulse wave data acquired by the air sucking action.

23. The pressure predicting method as set forth in claim 13, further comprising the step of:
detecting a body motion from the variation condition of the pulse wave signals.

24. The pressure predicting method as set forth in claim 23, further comprising the step of:
correcting the predicted pressure by removing the body motion detected from the pulse wave signals.

25. The pressure predicting method as set forth in claim 23, wherein the body motion is detected by analyzing frequencies of the pulse wave signals.

26. An examining method executed by a computer, wherein a medical treatment effect as to a sleep apnea syndrome or an upper airway resistance syndrome is confirmed by employing the pleural pressure predicted by the pressure predicting method as set forth in claim 13.

* * * * *